(12) United States Patent
Orbe Lopategui et al.

(10) Patent No.: US 8,541,370 B2
(45) Date of Patent: Sep. 24, 2013

(54) USE OF MATRIX METALLOPROTEINASE-10 (MMP-10) FOR THROMBOLYTIC TREATMENTS

(75) Inventors: Josune Orbe Lopategui, Navarra (ES); Jose Antonio Rodriguez Garcia, Navarra (ES); Jose Antonio Paramo Fernandez, Navarra (ES); Rosario Serrano Vargas, Navarra (ES)

(73) Assignee: Proyecto de Biomedicina Cima, S.L., Pamplona (Navarra) (ES)

( * ) Notice: Subject to any disclaimer, the term of this patent is extended or adjusted under 35 U.S.C. 154(b) by 254 days.

(21) Appl. No.: 12/861,357

(22) Filed: Aug. 23, 2010

(65) Prior Publication Data

US 2011/0091436 A1    Apr. 21, 2011

Related U.S. Application Data

(63) Continuation-in-part of application No. 12/449,748, filed as application No. PCT/ES2008/000072 on Feb. 11, 2008, now abandoned.

(30) Foreign Application Priority Data

Feb. 26, 2007   (ES) .................................. 200700501

(51) Int. Cl.
*A61K 38/36* (2006.01)
(52) U.S. Cl.
USPC ........................................................ 514/14.9
(58) Field of Classification Search
None
See application file for complete search history.

(56) References Cited

FOREIGN PATENT DOCUMENTS

| EP | 1 060 747 | 12/2000 |
|----|-----------|---------|
| WO | 03/028756 | 4/2003 |

OTHER PUBLICATIONS

International Search Report issued Jul. 1, 2008 in International (PCT) Application No. PCT/ES2008/000072.
N. Hiraoka et al., "Matrix Metalloproteinases Regulate Neovascularization by Acting as Pericellular Fibrinolysins", Cell, vol. 95, pp. 365-377, Oct. 30, 1998.
J. Orbe et al., "Independent association of matrix metalloproteinase-10, cardiovascular risk factors and subclinical atherosclerosis", Journal of Thrombosis and Haemostasis, vol. 5, pp. 91-97, Jan. 2007.
Baker, William F., "State-of-the-Art Review: Thrombolytic Therapy", Clin. Appl. Thrombosis/Hemostasis, 2002, 8(4): 291-314.
H. White et al., "Effect of Intravenous Streptokinase on Left Ventricular Function and Early Survival After Acute Myocardial Infarction", The New England Journal of Medicine, 1987, 317(14): 850-855.
N. Suwanwela et al., "Acute Ischemic Stroke: Overview of Recent Therapeutic Developments", The Annual Review of Medicine, 2007, 58: 89-106.
P. Armstrong et al., "Fibrinolysis for Acute Myocardial Infarction: Current Status and New Horizons for Pharmacological Reperfusion, Part 1", Circulation, 2001, 103: 2862-2866.
M. Brouwer et al., "Adjunctive Treatment in Patients Treated with Thrombolytic Therapy", Heart, 2004, 90: 581-588.
T. Cheng et al., "Activated Protein C Inhibits Tissue Plasminogen Activator-Induced Brain Hemorrhage", Nature Medicine, 2006, 12(11): 1278-1285.
A. Bini et al., "Characterization of Stomelysin 1 (MMP-3), Matrilysin (MMP-7), and Membrane Type 1 Matrix Metalloproteinase (MT1-MMP) Derived Fibrin(ogen) Fragments D-Dimer and D-like Monomer: $NH_2$-Terminal Sequences of Late-Stage Digest Fragments", Biochemistry, 1999, 38(42): 13928-13936.
M. Madlener et al., "cDNA Cloning and Expression of the Gene Encoding Murine Stomelysin-2 (MMP-10)", Gene, 1997, 202:75-81.
H. Nakamura et al., "Activation of the Precursor of Human Stomelysin 2 and it's Interactions with Other Matrix Metalloproteinase", Eur. J. Biochem., 1998, 253: 65-75.
O. Rechardt et al., "Stromelysin-2 is Upregulated During Normal Wound Repair and is Induced by Cytokines", Journal of Investigative Dermatology, 2000, 115: 778-787.
D. Li et al., "Regulated Expression of Collagenases MMP-1, -8, and -13 and Stromelysins MMP-3, -10, and -11 by Human Corneal Epithelial Cells", Invest. Opthalmol. & Vis. Sci. (IVOS), 2003, 44(7): 2928-2936.
I. Montero et al., "C-Reactive Protein Induces Matrix Metalloproteinase-1 and -10 in Human Endothelial Cells: Implications for Clinical and Subclinical Atherosclerosis", Journal of the American College of Cardiology, 2006, 47(7): 1369-1378.
W. Saunders et al., "MMP-10 Activation by Serine Proteases and MMP-10 Induces Human Capillary Tubular Network Collapse and Regression in 3D Collagen Matrices", Journal of Cell Science, 2005, 118(10): 2325-2340.
S. Chang et al., "Histone Deacetylase 7 Maintains Vascular Integrity by Repressing Matrix Metalloproteinase 10", Cell, 2006, 126: 321-334.
C. Longstaff et al., "Understanding the Enzymology of Fibrinolysis and Improving Thrombolytic Therapy", FEBS Letters, 2005, 579: 3303-3309.
P. Von Dem Borne et al., "Feedback Activation of Factor XI by Thrombin in Plasma Results in Additional Formation of Thrombin that Protects Fibrin Clots from Fibrinolysis", Blood, 1995, 86(8): 3035-3042.
Edwards, Neil. "Methods for Improving the Sensitivity and Specificity of the Fibrin Plate", J. Clin. Pathol., 1972, 25: 335-337.
C. Lombard et al., "Assays of Matrix Metalloproteinase (MMPs) Activities: A Review", Biochimie, 2005, 87: 265-272.

*Primary Examiner* — Sandra Saucier
(74) *Attorney, Agent, or Firm* — Wenderoth, Lind & Ponack, L.L.P.

(57) ABSTRACT

The present invention relates to the use of matrix metalloproteinase MMP-10 in the preparation of a pharmaceutical composition useful for thrombolytic therapy, it also being possible for said composition to contain a plasminogen activator. Additionally, the present invention relates to said pharmaceutical composition for the treatment of thrombotic disorders.

14 Claims, 10 Drawing Sheets

A

B

USE OF MATRIX METALLOPROTEINASE-10 (MMP-10) FOR THROMBOLYTIC TREATMENTS

This application is a Continuation-In-Part of U.S. application Ser. No. 12/449,748, filed Oct. 7, 2009 now abandoned, which is a national stage applicatioin of International application No. PCT/ES2008/000072, filed Feb. 11, 2008.

FIELD OF THE INVENTION

This invention relates to pharmaceutical compositions which include matrix metalloproteinase-10 (MMP10) and, more specifically, a combination of MMP-10 and a plasminogen activator, and the use thereof for thrombolytic therapy and treatment.

STATE-OF-THE-ART PRIOR TO THE INVENTION

The haemostatic system is the system in charge of maintaining circulatory flow and preventing hemorrhage in response to vascular attack. Physiological hemostasis is controlled both by the mechanisms which promote coagulation and fibrin formation, as well as those which favor the degradation thereof or fibrinolysis. Excessive activation of coagulation or a defect in fibrinolysis gives rise to the formation of clots which block the blood vessels (intravascular thrombosis), causing ischemia and necrosis. However, an overall situation of hyperfibrinolysis will favor the onset of hemorrhages.

Cardiovascular diseases of an atherothrombotic nature are today the main cause of morbid-mortality. Within this group of diseases, thrombotic processes are the main mechanism giving rise to acute cardiovascular events of major clinical importance, such as acute myocardial infarction (MI) or cerebrovascular accident (stroke).

Therefore, all of the strategies for treating cerebrovascular accidents and thrombotic events in general must necessarily promote the rapid rerouting of the arterial passage blocked by the clot in order to restore blood flow to the tissues and thus prevent any greater damage. This is what is commonly known as thrombolytic therapy.

Given that fibrinolysis is the underlying biochemical process of thrombolysis, thrombolytic therapy seeks, first of all, to favor the degradation of the fibrin network which is holding the clot together.

Given that plasmin is the enzyme which catalyzes the lysis and degradation of fibrin, the first objective for achieving a rapid dissolving of the clot is to maximize the generation of plasmin.

For this purpose, the use of plasminogen activators, capable of activating the conversion of the plasminogen (inactive proenzyme) into active plasmin: tissue plasminogen activator (tPA), urokinase plasminogen activator (uPA) or other similar agents was introduced as of 1980.

Baker [Clin. Appl. Thrombosis/Hemostasis, 2002; 8:291-314] conducts a review of the state-of-the-art in thrombolytic therapy and of the thrombolytic agents in use or in development, the clinical application thereof, as well as advantages and drawbacks. In this document, Baker also sets out the characteristics which an ideal thrombolytic agent should have: 1) fast-acting thrombolysis, for the rapid restoring of arterial or venous flow; 2) fibrin specificity, so that the fibrinolysis will be confined to the areas of acute thrombosis with a reduced systemic fibrinolysis; 3) sustained action over time; 4) clot specificity so as to prevent effects on the fibrinogen, other proteins involved in coagulation and not to alter primary hemostasis; 5) no side-effects; and 6) low cost.

In the case of acute myocardial infarction and of acute cerebrovascular ischemia (stroke), the success of the thrombolytic treatment leads to an increase in the survival of the patients and a better recovery of the function of the ischemic tissue [White H D et al.; N. Engl. J. Med., 1987; 317:850-855]; [Suwanwela N and Koroshetz W J; Annu. Rev. Med., 2007; 58:89-106]. Unfortunately, fibrinolytic treatment has failures and side-effects.

Almost 40% of the patients with acute myocardial infarction do not respond to fibrinolytic treatment and do not achieve an optimum rerouting of the artery blocked by the thrombus [Armstrong P W and Collen D; Circulation, 2001; 103:2862-2866].

To solve this problem, instead of pharmacological thrombolysis, primary percutaneous angioplasty is currently being used as reperfusion treatment more effective than thrombolytic treatment in terms of reducing the death rate, reinfarction and hemorrhage. It is not however possible to use angioplasty in many cases (no hemodynamics laboratory available or geographical distance can not be assumed) and it is then when thrombolytic treatment is performed. Therefore, it is desirable that new treatment strategies be developed which make it possible to improve the effectiveness of the thrombolytic treatment, for example, prehospital fibrinolytic treatment, new thrombolytic agents (tenecteplase), or new pharmacological combinations (i.e., reduce the fibrinolytic agents to half the dose and add a GP IIb/IIIa platelet receptor blocker [Brouwer M A et al., Heart, 2004; 90:581-588]. A considerable death rate also exists related to fibrinolytic treatment due to hemorrhagic complications; specially hemorrhage of the central nervous system and major hemorrhages, with a 2%-14% incidence.

In the case of acute cerebrovascular ischemia, the thrombolytic treatment with recombinant tPA within the first three hours following the onset of the symptoms is the only scheme which has shown itself to be somewhat effective. Unfortunately, in 25%-30% of the cases, the treatment fails, the clot does not lyse, and the blocked artery does not become permeable. Additionally, the treatment with tPA has a high percentage of hemorrhagic complications (up to 5% entail symptomatic hemorrhage), and many physicians fear this complication. For that reason, a large majority of patients who could benefit from this treatment does not receive it. Another problem related to administering tPA, potentially more serious than the risk of hemorrhaging, is the toxicity on the central nervous system which is many times responsible for the therapeutic failure [Cheng T. et al., Nat. Med., 2006; 12:1278-1285]. Therefore, reducing the risk of hemorrhaging from administering tPA could change the perception of the safety of this drug and increase its use. Therefore, it still continues to be necessary to select therapeutic agents and combinations which will make it possible to reduce the toxicity of the tPA either directly or indirectly, by lowering the dose necessary for treating stroke.

Given that there are enzymes different from plasmin which can directly degrade fibrinogen and fibrin, research is also being done of their potential use for thrombolytic treatment. These enzymes include proteases endogenous to leukocytes (elastase and cathepsin G), snake venom or leech proteases or proteases from some bacteria.

In EP1060747, the use of fibrinolytic matrix metalloproteinases is described which show a significant activity for proteolytically cleaving and degrading fibrin and fibrinogen. These fibrinolytic metalloproteinases include MMP-2 (gelatinase A), MMP-3 (stromelysin 1), MMP-7 (matrilysin), MMP-9 and very particularly membrane-type matrix metalloproteinase MMP-MT1. Months later, Bini et al. compiled and expanded upon these same findings [Biochemistry, 1999; 38: 13928-13936]. However, neither in these nor in other later works are data provided concerning the effectiveness of these fibrinolytic are matrix metalloproteinases in the lysis and degradation of the fibrin which forms thrombi, either for achieving a more rapid dissolving of the clot, or rather for providing a greater selectivity for the degradation of the fibrin in the clot respecting the systemic fibrinogen.

The objective of the present invention is to provide alternative therapeutic compositions and combinations for thrombolytic treatment which will favor the lysis of the clots by means of a selective degradation of the fibrin and which will aid in minimizing the adverse effects related to other thrombolytic treatments (hemorrhage, toxicity, etc.).

DETAILED DESCRIPTION OF THE INVENTION

Figure 1:
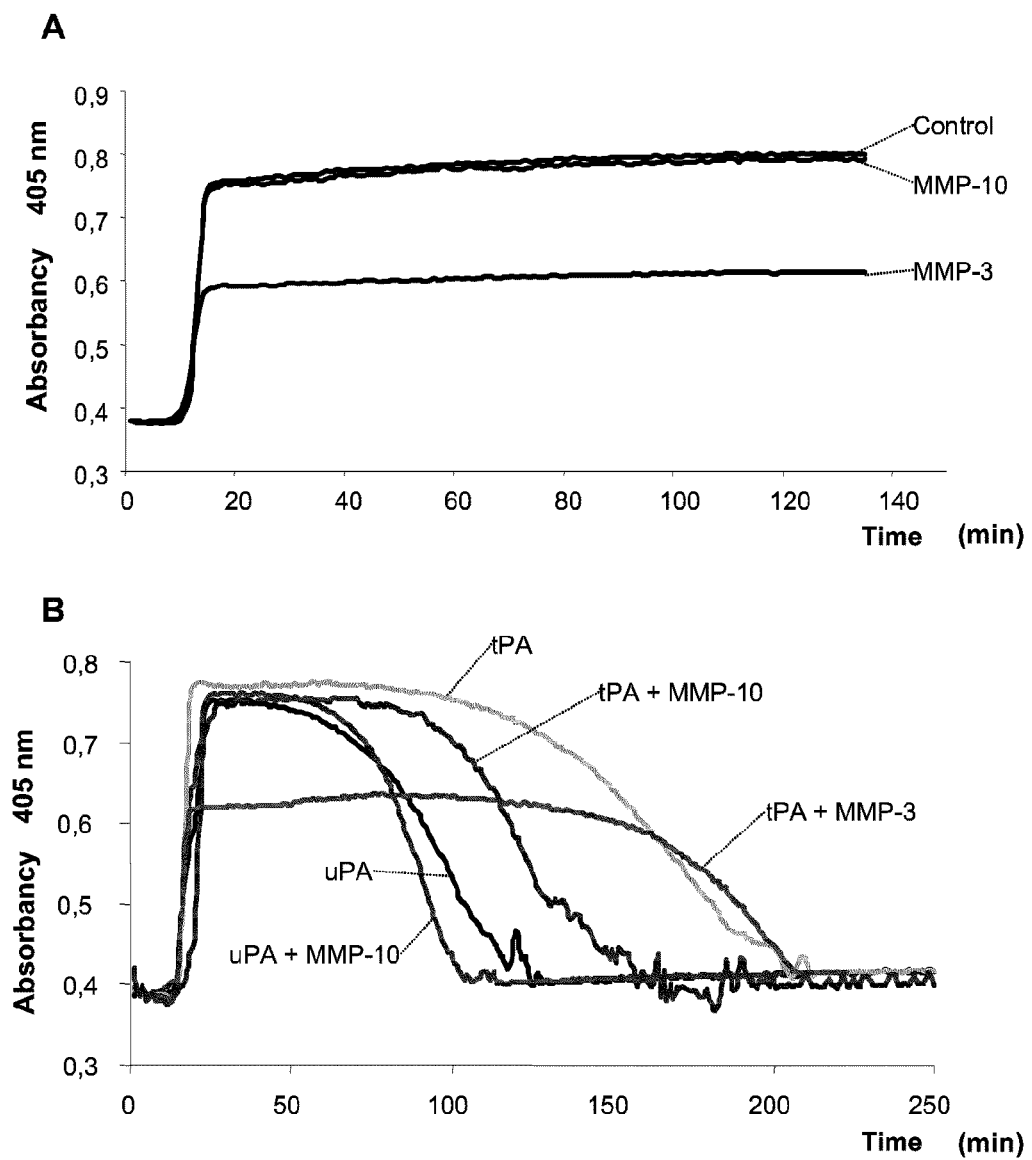
FIG. 1. Recalcified plasma turbidimetry test given as the absorbance values at 405 nm compared to the time the experiment lasts in minutes. A: the graph shows the differences in clot formation (maximum absorbance) of the plasma alone (control) or in the presence of MMP-10 (200 nM) or MMP-3 (200 nM). B: The graph depicts the formation and lysis of the fibrin clot of the recalcified plasma in the presence of tPA plasminogen activators (30 U/ml) and uPA (135 U/ml) alone or combined with MMP-10 (200 nM) and also in the presence of an equivalent dose of MMP-3 (200 nM) combined with tPA (30 U/ml).

This invention relates, firstly, to the use or utilization of matrix metalloproteinase-10 (MMP-10) in the preparation of a medicament for thrombolytic therapy and treatment.

MMP-10, or stromelysin-2, is located in chromosome 11 and is expressed by different cell types, such as the endothelial cells, monocytes and fibroblasts [Madlener M and Werner S; Gene, 1997; 202:75-81]. It is known that it can be activated by plasmin, kallikrein, tryptase, elastase and cathepsin G and can degrade a wide range of substrates of the extracellular matrix, such as aggrecan, elastin, fibronectin, gelatin, laminin, tenascin-C, vitronectin and collagens type II, III, IV, IX, X and XI. Additionally, MMP-10 can activate other matrix metalloproteinases, such as proMMP-1, -3, -7, -8 and -9 [Nakamura H et al., Eur. J. Biochem., 1998; 253: 67-75].

It is likewise known that MMP-10 is involved in different physiological processes, such as bone growth or wound healing. It is also found overexpressed in corneas of patients with diabetic retinopathy and has been related to some types of carcinoma, as well as lymphoid tumors. Different in vitro studies have shown that, in keratinocyte cultures, the expression of MMP-10 can be induced both by growth factors (epidermal growth factor of keratinocytes or TGF-beta), as well as by proinflammatory cytokines (TNF-alfa, IL-1beta) [Rechardt O et al., J. Invest. Dermatol., 2000; 115:778-787]; [Li de Q et al.; Invest. Ophthalmol. Vis. Sci. 2003; 44 :2928-2936].

Also in publications prior to this invention, it has been described that MMP-10:

- may be an inflammatory biomarker of vascular risk [Montero I et al.; J. Am. Coll. Cardiol., 2006; 47:1369-1378] [Orbe J et al.; J. Thromb. Haemost.; 2007; 5: 91-97];
- is induced in endothelial cells which are forming capillaries in 3D collagen matrixes and is involved in the regression of the formation of capillaries by means of the activation of MMP-1 [Saunders WB et al.; J. Cell. Sci., 2005; 118: 2325-2340]; and that
- it plays a fundamental role in maintaining the intracellular bonds which preserve vascular integrity in angiogenesis and remodeling processes [Chang S et al.; Cell, 2006; 126:321-334].

In the present invention, the effect of MMP-10 and of MMP-3 on the formation and lysis of clots in human plasma, as well as on other in vitro models of polymerized fibrin degradation has been tested.

The inventors have been able to prove that MMP-10 does not have any direct thrombolytic activity and that it is not capable of degrading fibrinogen or fibrin by itself. Surprisingly, they have also proven that, in the presence of thrombolysis-activating agents, particularly plasminogen activators, MMP-10 favors the dissolving of the fibrin clots and shortens lysis time. MMP-10 therefore acts as a facilitator or adjuvant of the thrombolytic action of other thrombolysis activators.

On the contrary, a fibrinolytic matrix metalloproteinase such as MMP-3, which has a direct proteolytic activity on fibrin and fibrinogen, does not shorten the clot lysis times which is provided by the thrombolysis activators by themselves.

Within the context of this invention, "thrombolytic therapy" is understood as being that therapy which, in clinical situations of ischemia of thrombotic origins, the reperfusion or restoring of blood flow by means of the lysis or rapid dissolving of the clots which are blocking the circulation and jeopardizing organ function, is being sought. These clinical situations include, in particular, thrombolytic therapy in acute myocardial infarction, in cerebral thromboses (more particularly acute cerebral infarction or stroke), as well as other venous thromboembolisms (i.e. pulmonary embolism or deep-vein thrombosis) and peripheral arterial thrombosis.

This invention relates, more particularly, to the use or utilization of MMP-10 and a plasminogen activator in the preparation of a medicament or pharmaceutical composition for thrombolytic therapy and treatment by means of simultaneous, separate or sequential administration.

Within the context of this invention, a plasminogen activator is a compound which activates the conversion of inactive plasminogen into plasmin by means of the cleavage of the peptide bond between Arg560 and Val1561 of the plasminogen. In particular, these plasminogen activators include: urokinase (uPA), tissue plasminogen activator (tPA), streptokinase and staphylokinase.

In one particular embodiment of this invention, the plasminogen activator is tPA.

In another particular embodiment, the plasminogen activator is uPA.

In yet another particular embodiment, a derivative or fragment of the aforementioned plasminogen activators can be used as the plasminogen activator which retains its ability to cleave and activate the plasminogen for which the effect of facilitating the MMP-10 is effective. An expert in the field can readily see this effect by himself, for example by means of in vitro clot formation and lysis tests such as those described in examples 1 to 4 of this invention. Longstaff and Thelwell [FEBS Letters, 2005; 579: 3303-3309] review some of the plasminogen activators currently in use or in development, from among which an expert can choose, for using them in combination with MMP-10 according to the present invention.

Advantageously, on not interacting with the circulating fibrinogen/fibrin and being capable of facilitating the action of the plasminogen activators, MMP-10 would make it possible to reduce the dose of the thrombolytic by maintaining the effectiveness for lysing the clot, but without inducing systemic fibrinolysis, which would entail a great incidence of hemorrhaging-related complications. Similarly, it would make it possible to reduce the toxicity resulting from the thrombolytic treatment with agents such as tPA.

According to another aspect, the present invention also relates to a pharmaceutical combination which comprises, separately, or in one same composition, MMP-10 and a plasminogen activator, mixed with pharmaceutically-acceptable excipients or vehicles. The plasminogen activator in the combination may be any of those mentioned hereinabove.

The aforesaid combination is useful for thrombolytic therapy and treatment in mammals, particularly in humans, in any of the aforementioned clinical conditions stated hereinabove.

The origins of MMP-10 and of the plasminogen activator in the pharmaceutical combination are not a critical aspect of this invention. The active ingredients may be obtained by extraction and purification from biological fluids or tissues by means of recombinant or genetic engineering procedures or any other conventional technique.

Depending on the circumstances, to be determined in each case by means of the customary pharmacological and clinical tests, the active ingredients of the pharmaceutical combination can be administered simultaneously, separately or sequentially.

According to one embodiment of the invention, the active ingredients (MMP-10 and plasminogen activator) can be contained in one some pharmaceutical composition. In other cases, the active ingredients can be contained in separate pharmaceutical compositions, each one thereof in its own container mixed with pharmaceutically-acceptable excipients or vehicles.

The pharmaceutical compositions with the active ingredients, whether one or more, can be formulated in both solid form (i.e. freeze-dried in vials to later be reconstituted in a suitable solution) or also in liquid form.

In one particular embodiment, these compositions with the active ingredients constitute a kit for thrombolytic therapy or treatment which may optionally include other components, such as: containers with solutions for reconstituting the active ingredients, cannulas, drip bags with physiological serum for intravenous application and instructions for use, etc.

The pharmaceutical compositions with the active ingredients may be administered by any suitable route, for example, orally, parenterally, rectally or topically, for which they will include the pharmaceutically-acceptable excipients and vehicles necessary for the formulation of the desired form of administration.

In one particular embodiment, administration is parenteral, for example by intravenous injection, or administered locally by catheterization for in situ administration in the near vicinity of the clot.

When the pharmaceutical combination is for administering separately, both active ingredients may also be contained in pharmaceutical compositions suitable for administering by different routes.

The quantities of MMP-10 and of plasminogen activator which may be present in the compositions of the pharmaceutical combination provided by this invention may vary within a broad range, but always in therapeutically effective quantities.

The dosage for each thrombolytic treatment protocol with the compositions of the pharmaceutical combination of this invention will depend on numerous factors, including the patient's age, condition, the severity of the clinical condition to be treated, the route and frequency of administration and of the plasminogen activator which is going to be administered in each case.

In one typical embodiment, the quantities and doses of the plasminogen activator will be smaller than those which would be used for this same plasminogen activator when MMP-10 is not included in the therapeutic combination. On the other hand, the quantities of MMP-10 will be adjusted in terms of the effect one wishes to achieve: greater thrombolytic effectiveness by maintaining the plasminogen activator dosage; or a reduction of the plasminogen activator dose maintaining the thrombolytic effectiveness.

In another aspect, this invention relates to a pharmaceutical combination or a kit of the invention, as have already been described, for thrombolytic therapy.

In another additional aspect, the invention also relates to a method of treatment and thrombolytic therapy consisting of administering to the patient a therapeutically effective quantity of MMP-10. In one particular embodiment, said method also consists of administering of a plasminogen activator, by simultaneous, separate or sequential administration. Any of the aforementioned pharmaceutical compositions and combinations could be used for this method.

The following examples illustrate this invention and must not be considered limiting of the scope thereof.

EXAMPLES OF THE INVENTION

The examples illustrate the effects on the fibrinolytic and thrombolytic activity of the MMP-10 and MMP-3 matrix metalloproteinases, either directly or in combination with some plasminogen activators: urokinase (uPA) and tissue plasminogen activator (tPA).

The following has been employed for the examples:

Recombinant MMP-10, obtained as 58 kDa enzyme with 20%-30% mature 48 kDa enzyme (R&D Systems, 910-MP, Abingdon, UK), which was reconstituted with TCNB buffer (50 mM Tris-HCl, pH 7.5, 10 nM $CaCl_2$, 150 mM NaCl, 0.05% Brij35).

Recombinant MMP-3, obtained as 52 kDa enzyme (R&D Systems, 513-MP, Abingdon, UK), supplied in a solution with 12.5 nM Tris, 5 nM $CaCl_2$, 0.025% Brij35 and 50% glycerol.

Urokinase (uPA) (Vedim Pharma SA; 628602, Barcelona, Spain).

Recombinant plasminogen tissue activator (tPA) (Boerhinger Ingelheim; 985937 Actilyse®, Ingelheim, Germany).

For the evaluation of the thrombolytic activity, a turbidimetric method was used for monitoring the formation and lysis of the fibrin clot on plasma samples according to the protocol previously described by von dern Borne et al., [Blood, 1995; 86:3035-3042].

On the other hand, for evaluating the activity on the fibrin lysis, tests were conducted on fibrin plates following the procedure described by Edward [J. Clin. Path., 1972; 25: 335-337].

Example 1

Effect of MMP-10 and MMP-3 on Clot Formation and Lysis

As previously mentioned hereinabove, by means of the procedure described by von darn Borne et al., an evaluation was conducted of the effect of MMP-10 and MMP-3 on the haemostatic system. In this method, the changes in turbidity/absorbency during the formation and lysis of clots are assessed as an indicator of the length of both of these processes. The turbidity is measured by reading the absorbance at 405 nm during the clot formation and lysis phases using a photometric reader, which, in our case, was an ELISA reader (Fluostar Optima, BMG Labtech). The increase in turbidity/absorbance indicates the formation of the fibrin clot, whilst the lessening of this parameter indicates the lysis of the clot.

For the formation of the clot, 75 µl citrated plasma, 75 µl HEPES buffer (25 mM HEPES, 137 mM NaCl, 3.5 mM KCl, 6 mM $CaCl_2$, 1.2 mM Mg $Cl_2$, and 0.1% BSA, pH=7.5) and 10 µl $CaCl_2$ 150 mM were mixed in a micro-plate well. The plate was incubated to 37° C. and the absorbance at 405 nM measured for 2 hours every 30 seconds.

To study the effect of the MMP-10 on clot formation, activated MMP-10 (50, 100 and 200 nM) was added to the initial plasma and HEPES buffer mixture. Prior to its use in the experiments, the MMP-10 was activated by means of heat treatment at 37° C. for 1 hour.

In parallel tests, the effect on clot formation was also analyzed with the MMP-3 (200 nM). In this case, the MMP-3 was previously activated with 1 mM p-aminophenylmercury acetate (APMA, 164610, EMD Biosciences, La Jolla, USA) at 37° C. for 24 h.

As is shown in FIG. 1A, the MMP-10 did not induce any changes in either the speed of the clot formation or in the maximum degree of turbidity reached with any of the doses employed (Table 1). However, the MMP-3 induced a 50% drop in the maximum absorbency/turbidity of the clot formed, probably due to it direct proteolytic action on the fibrinogen.

These results show that the MMP-10, unlike what was described for the MMP-3, does not alter the clot-formation rate on not displaying any fibrinolytic activity regarding the fibrinogen.

Afterwards, a study was conducted of the fibrin clot lysis rate and, to this end, as in the immediately preceding section hereinabove, recalcified plasma in HEPES buffer was used, to which, simultaneously with the MMP-10 (or MMP-3, as the case may be), a plasminogen activator was added in order to select either 30 U/ml of tissue plasminogen activator (tPA) or 135 U/ml urokinase (uPA) at the beginning of the turbidimetry.

The concentrations of tPA and uPA to be used were determined in prior dose-response studies, where the dose of choice was that which completely lyses the fibrin clot within a two-hour (2 h) time period.

As is shown in FIG. 1B and Table 1, the MMP-10 in absence of tPA and uPA did not cause the lysis of the fibrin clot, whilst in the presence of the tPA or uPA activators, it induced a significant increase in the fibrin clot lysis rate. With the maximum dose of MMP-10 tested (200 nM), the shortening of the lysis time (time at which half of the clot lyses) was 15 min (52.9 min vs. 68.3 min, p<0.01) in the presence of tPA and 5 min in the presence of uPA (42 min vs. 47.5 min, p<0.05). This reduction in the lysis time means a 20% shortening in the presence of tPA and a 10% shortening with the uPA.

To the contrary, the MMP-3 did not change the clot lysis rate in the presence of tPA.

These findings indicate that MMP-10, unlike MMP-3, is not capable of digesting the fibrin but does heighten the fibrinolytic effect of the plasminogen activators and of the fibrinolysis (tPA or uPA). On not having the ability to act on the endogenous fibrinolysis, the MMP-10 would prevent or attenuate the onset of hemorrhages, which makes it a good candidate for being used as a coadjuvant of thrombolytic therapy.

TABLE 1

Fibrin clot lysis time (given in minutes), in the presence of plasminogen activators (tPA or uPA).

|  | TPA 30 U/ml | tPA 20 U/ml | tPA 15 U/ml | uPA 135 U/ml |
|---|---|---|---|---|
| Control | 68.3 | 102.0 | 125.3 | 47.5 |
| MMP-10 50 nM | 65.5 | — | — | — |
| MMP-10 100 nM | 61.2 | — | — | — |
| MMP-10 200 nM | 52.9 | 84.7 | 108.7 | 42.0 |
| MMP-3 200 nM | 76.3 | — | — | — |
| Anti-MMP-10 (MAb) | No lysis | — | — | No lysis |
| (IgG) Isotype control | 74.3 | — | — | 48.3 |

Example 2

Effect of MMP-10 on Fibrin Degradation

According to the aforementioned Edward procedures, a study was made of the effect on fibrin lysis by measuring the halo or lysis area which is caused on a polymerized fibrin plate.

The fibrin plates are prepared from a 6 mg/ml human fibrinogen solution (Sigma, F3879, Saint Louis, Mo., USA) in veronal buffer (BioWhittaker, 12-624E, Cambrex, Md., USA) at 37° C., which is filtered and to which an equal volume of $CaCl_2$ (50 mM) is added. This solution (6 ml) is mixed with 1 international unit (NIH units) thrombin (Enzyme Research Lab; HT1200a, Swansea, UK) and is left to polymerize for 6 h.

To assess the fibrinolytic capacity, tPA (1 U/ml), MMP-10 (200 nM) or a combination of the two were added to different fibrin plates.

Figure 2:
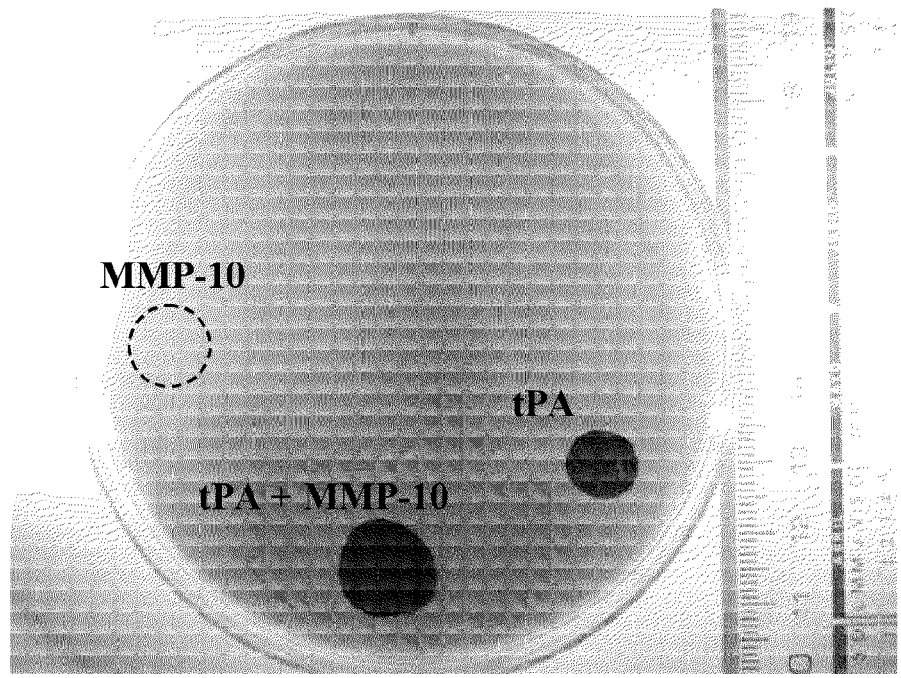
FIG. 2. Polymerized fibrin plate showing the lysis areas caused by the tPA (1 U/ml) and the MMP-10 (200 nM) individually, or added in combination with one another.

As is shown in FIG. 2, the MMP-10 alone did not cause lysis on the polymerized fibrin, whilst the tPA caused a marked halo. However, the combination of tPA and MMP-10 significantly increased the polymerized fibrin lysis area (188.6%), this being a fact which confirms the fibrinolysis-facilitating effect that MMP-10 has in combination with plasminogen activators as fibrinolytic agents.

Example 3

Effect of Coadministration of MMP-10 and a Thrombolytic Agent (tPA or uPA) on Clot Lysis Given the effect of the MMP-10 on the tPA-included lysis, the question was posed of ascertaining whether it is possible to reduce the dose of tPA (which entails hemorrhage and neurological toxicity-related problems) and use MMP-10 as a coadjuvant for achieving the same thrombolytic effect.

Figure 3:
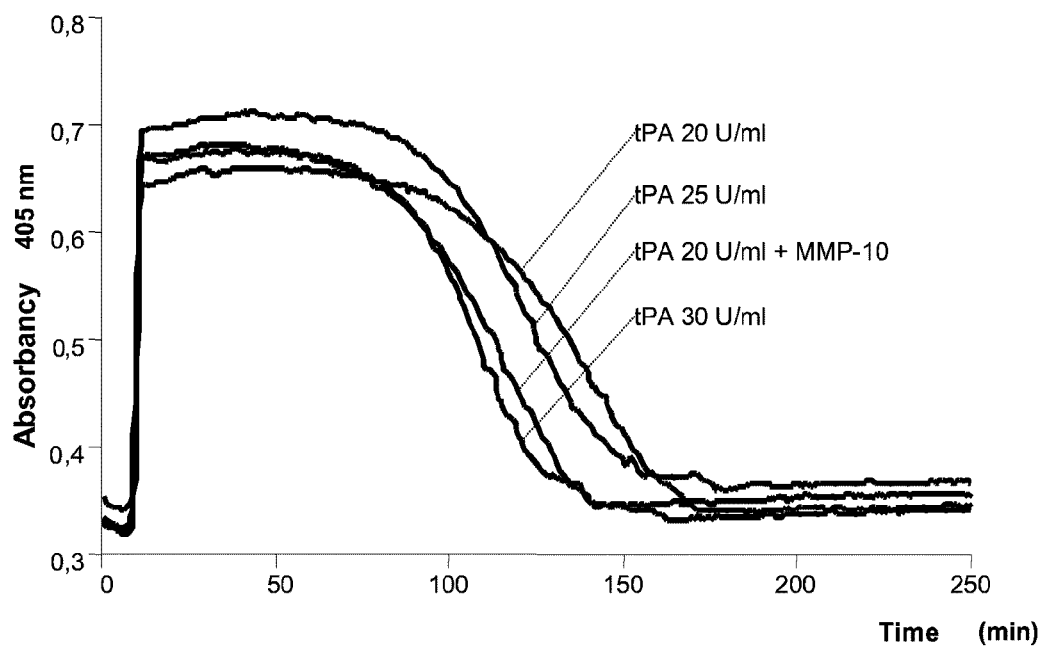
FIG. 3. Turbidimetry test showing the difference in the lysis time of the fibrin clot at different doses of tPA (20, 25 and 30 U/ml). The combination of MMP-10 (200 nM) and tPA (20 U/ml) shortens the lysis time as compared to the activator by itself.

In the turbidimetry test conducted following the procedure described in Example 1 hereinabove, we found that the presence of MMP-10 (200 nM) in combination with the tPA makes it possible to reduce the dose of tPA by 33% (from 30 to 20 U/ml), achieving the same clot lysis time (FIG. 3, table 1).

This result indicates that in a subject who needs thrombolytic therapy, MMP-10 provides the way to increase the fibrinolysis and clot lysis by simultaneously lowering the dose of tPA and therefore, minimizing the hemorrhagic and toxicity-related problems caused by this drug.

Example 4

Inhibition of Clot Fibrinolysis and Lysis Induced by tPA with Anti-MMP-10 Antibodies According to the results of Examples 1 and 2, an analysis was made of the specificity of the effect of the MMP-10 on fibrin lysis in the clot induced by tPA by simultaneously adding different doses of active MMP-10 in the presence (1:2 ratio) and absence of a monoclonal antibody which blocks its activity (R&D systems, MAB9101, Abingdon, UK), or of IgG2B murine isotype control antibody (eBioscience, 16-4732, San Diego, Calif., USA) at the same concentration as the antibody.

Figure 4:
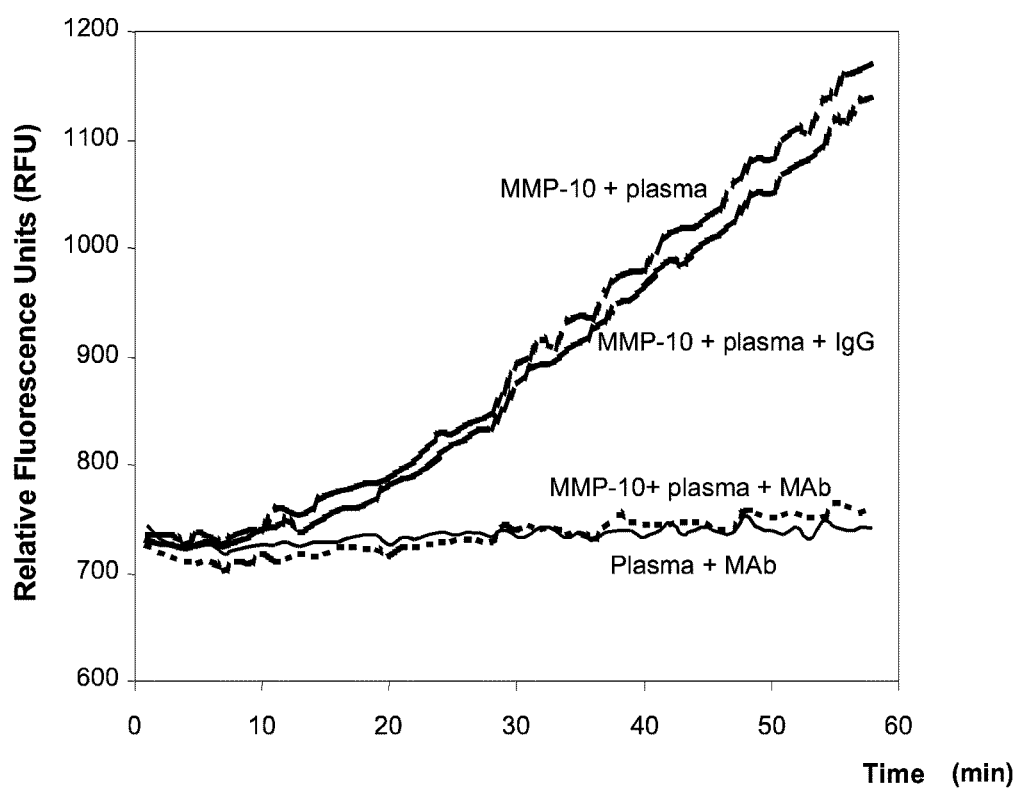
FIG. 4. Test of MMP-10 (100 nM) plasma activity with a fluorescent stromelysin substrate. The monoclonal antibody (MAb) concentration which inhibits the MMP-10 plasma activity was determined by means of the reduction in the slope of the substrate formation. As a control, an IgG isotype control antibody was used.

The enzyme:antibody ratio which blocks the activity of the enzyme was previously analyzed in an activity test for the MMP-10 on a microdish covered with an anti-MMP-10 antibody (R&D Systems, Clon110343) and using the fluorogenic stromelysin substrate (MCA-Arg-Pro-Lys-Pro-Val-Glu-Nval-Trp-Arg-Lys-[DNP]-$NH_2$) (R&D Systems; ES002, Abingdon, UK) [Lombard et al.; Biochimie, 2005; 87:265-272). The fluorescence (320 nm excitation and 405 nM emission) was measured on a spectrofluorimeter (SpectraMAX GeminiXS, Molecular Devices, Calif., USA) for 1 h, it having been found that the 1:2 ratio completely inhibits the concentration of active enzyme (FIG. 4).

Figure 5:
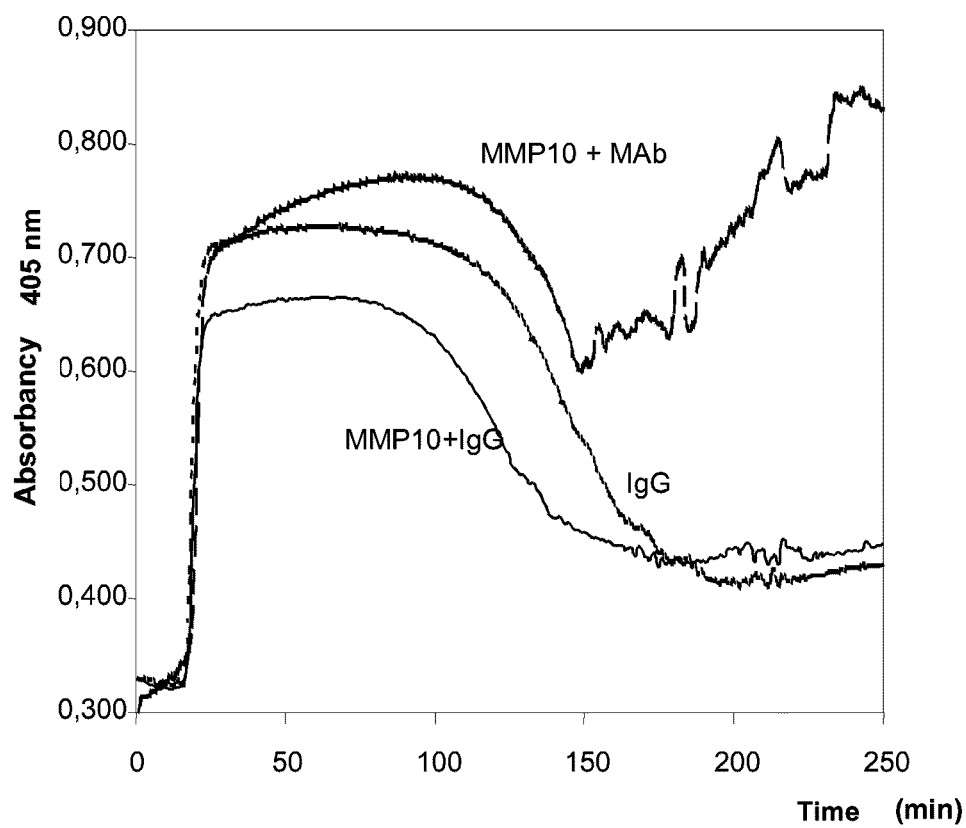
FIG. 5. Turbidimetry test of the plasma recalcified with MMP-10 (200 nM) in the presence or absence of a monoclonal antibody (MAb) which inhibits the activity of the MMP-10, and of an isotype (IgG) control antibody.

The results show the coadjuvant effect on the fibrinolysis to be MMP-10 specific, given that it reverses in the presence of the anti-MMP-10 antibody. This effect is quite remarkable when said antibody is added to block the endogenous activity of the plasma MMP-10 (FIG. 5). The results reveal that the absence of MMP-10 in the plasma prevents the lysis of the fibrin clot even in the presence of tPA or uPA (Table 1).

Figure 6:
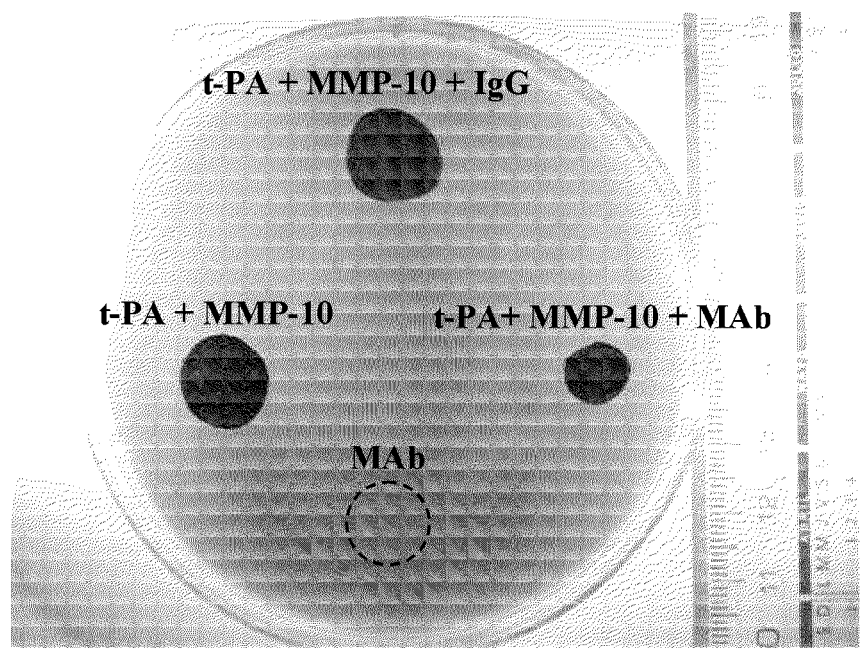
FIG. 6. Fibrin plate illustrating the differences in the lysis area caused by the tPA (1 U/ml) and the MMP-10 (200 nM) in the presence or absence of a monoclonal antibody which inhibits the activity of the MMP-10 (MAb) and the isotype control antibody (IgG).

These results were corroborated in the polymerized fibrin plate tests. As is shown in FIG. 6, in the presence of the anti-MMP-10 antibody, the lysis area caused by the tPA: MMP-10 combination is reduced (91.2% vs. 188:6%), whilst the control antibody has no effect (184.6%). This data confirm that employing an MMP-10 inhibitor antibody blocks the pharmacological dissolving of fibrin clots.

Example 5

Production of Recombinant Human MMP-10

Expression System for Human MMP-10

The full-length human MMP-10 was amplified using the following primers: 5'-ATGATGCATCTTGCATTCCTT-3' (SEQ ID NO: 1) (forward) and 5'-GCAATGTAACCAGCT-GTTACT-3' (SEQ ID NO: 2) (reverse), by using the KOD Hot Start DNA polymerase enzyme (Novagen). The insert was cloned into the pcDNA 3.1-V5-His (Invitrogen) expression vector, between the BstXI and the EcoRV sites in frame with a c-myc epitope and six histidines (His) tag in order to express the human MMP-10 fused with this tag at the C-terminal end. TOP 10 cells were transformed with the plasmid and its isolation from cell cultures was carried out with the Qiagen Plasmid Mini Kit (Qiagen) and then subjected to sequencing.

The purified plasmid was used to perform the HEK (Human Embryonic Kidney fibroblasts) cells transformation.

HEK cells were transformed with 4 μg of pcDNA 3.1-V5-His using Lipofectamine (Invitrogen). The transfected cells were grown in the presence of DMEM containing 2 mg/ml of the selective antibiotic geneticin (Calbiochem) to select the more efficient clones.

Once the selection was performed, supernatants were screened for the production of hMMP-10 by ELISA (R&D Systems) and Western blot with an anti-MMP10 antibody directed to the catalytic domain of the protein (MAB9101, R&D Systems).

The cell culture was expanded to grow in T-175 $cm^2$ flasks (Costar; "Cell Bind") and cells were cultured in low foetal bovine serum medium (Advanced DMEM; GIBCO).

Purification of Recombinant Human MMP-10

Every 48 hours the supernatants were collected and maintained on ice during filtration, and concentration (Vivaflow 200; cut off 30 kDa). Finally they were stored at $-20°$ C. until the purification process.

The ice-cold concentrated supernatant was applied to 1 ml Co-MAC column (Novagen). After washing the non-specifically retained proteins with binding buffer (20 mM Tris-HCl, 5 mM Imidazole and 500 mM NaCl; pH=7.9), bound proteins were eluted with elution buffer (20 mM Tris-HCl, 500 mM Imidazole and 500 mM NaCl; pH=7.9). Eluted fractions were pooled and subjected to an immunoaffinity chromatography in a HiTrap NHS-activated HP column (Amersham Biosciences, USA) coupled with an anti-His antibody (R&D systems). Non-specific proteins were removed from the column by washing with binding buffer (20 mM Tris-HCl and 500 mM NaCl; pH=7.5) and the hMMP-10 was eluted with Glycine 0.1 M pH=2.9. The different eluted fractions were concentrated, dialysed against TNB buffer (50 mM Tris-HCl pH=7.5, 150 mM NaCl and 0.05% Brij 35) and stored at $-80°$ C. The purity of the sample was analysed by sodium dodecyl polyacrilamide gel electrophoresis (SDS-PAGE) followed by staining with Gelcode Blue Stain Reagent (Thermo Scientific, USA).

All the purification steps were carried out using a FPLC System (GE Healthcare) at room temperature but maintaining the sample on ice and measuring the absorbance at 280 nm. Protein concentration of the sample was determined spectrophotochemically using a Nanodrop ND-1000 (Thermo Scientific, USA) and applying an extinction coefficient of 1,497 $M^{-1}$ $cm^{-1}$ based on the primary sequence of hMMP-10. The sample was also evaluated by Western blot with an anti-MMP10 antibody (R&D Systems)

Example 6

Effect of MMP-10 on Bleeding Time and Fibrinolysis

Bleeding time was determined in Mmp10$^{-/-}$ mice to assess whether MMP-10 functions in haemostasis in vivo. Further, we looked for differences in plasma fibrinolytic activity between WT and Mmp10$^{-/-}$ mice, producing euglobulin fractionated plasma and assaying it on fibrin plates.

Methods

Animals

MMP-10 null mice (Mmp10$^{-/-}$) generated by removing MMP-10 catalytic domain (exons 3 to 5) and crossbred for 10 generations with C57BL/6 mice, were obtained from WC. Parks (Center for Lung Biology, University of Washington, Seattle, Wash. 98109, USA) and bred in local animal facilities (Kassim et al., *Infect Immun* 2007;75(12):5640-50). Experiments were performed in accordance with European Communities Council Directives (86/609/EEC) guidelines for the care and use of laboratory animals and was approved by the Institutional Research Review Committee.

Tail Bleeding Assay

Wild-type C57Bl6 (n=15) (WT) and Mmp10$^{-/-}$ (n=15) mice (2 months old) were anaesthetised by intraperitoneal injection of ketamine (80 mg/kg) and xylazine (5 mg/kg), and maintained at 37° C. on heating pads. 5 mm of tail tip was removed using a scalpel blade and the tail tip bathed in 1 ml of sterile saline at 37° C. The time to cessation of bleeding was measured up to 30 minutes. Additional experiments were performed in Mmp10$^{-/-}$ (n=10) mice and WT mouse receiving active recombinant human MMP-10 (200 ng), tPA or saline through tail vein and bleeding time was recorded.

Fibrinolytic Activity of Plasma Euglobulins

Plasma euglobulins from WT and Mmp10$^{-/-}$ were obtained as follows: Pooled plasma (200 μL) was diluted 1:10 with distilled water and acidified to pH 5.9 with acetic acid. After 30 min on ice, the precipitate was centrifuged and redissolved in 200 μL Hepes buffer (pH 7.5). 25 μl of plasma euglobulin were pippeted on fibrin plate and further incubated at 37° C. for 18 h. The area of the lysis zones was determined as a measurement of fibrinolytic activity.

Statistical Analysis

Data from mice were analysed by the non-parametric Kruskall-Wallis test followed by the Mann-Whitney U test to compare different experimental groups. Continuous variables were expressed as mean±SD.

Results

Figure 7:
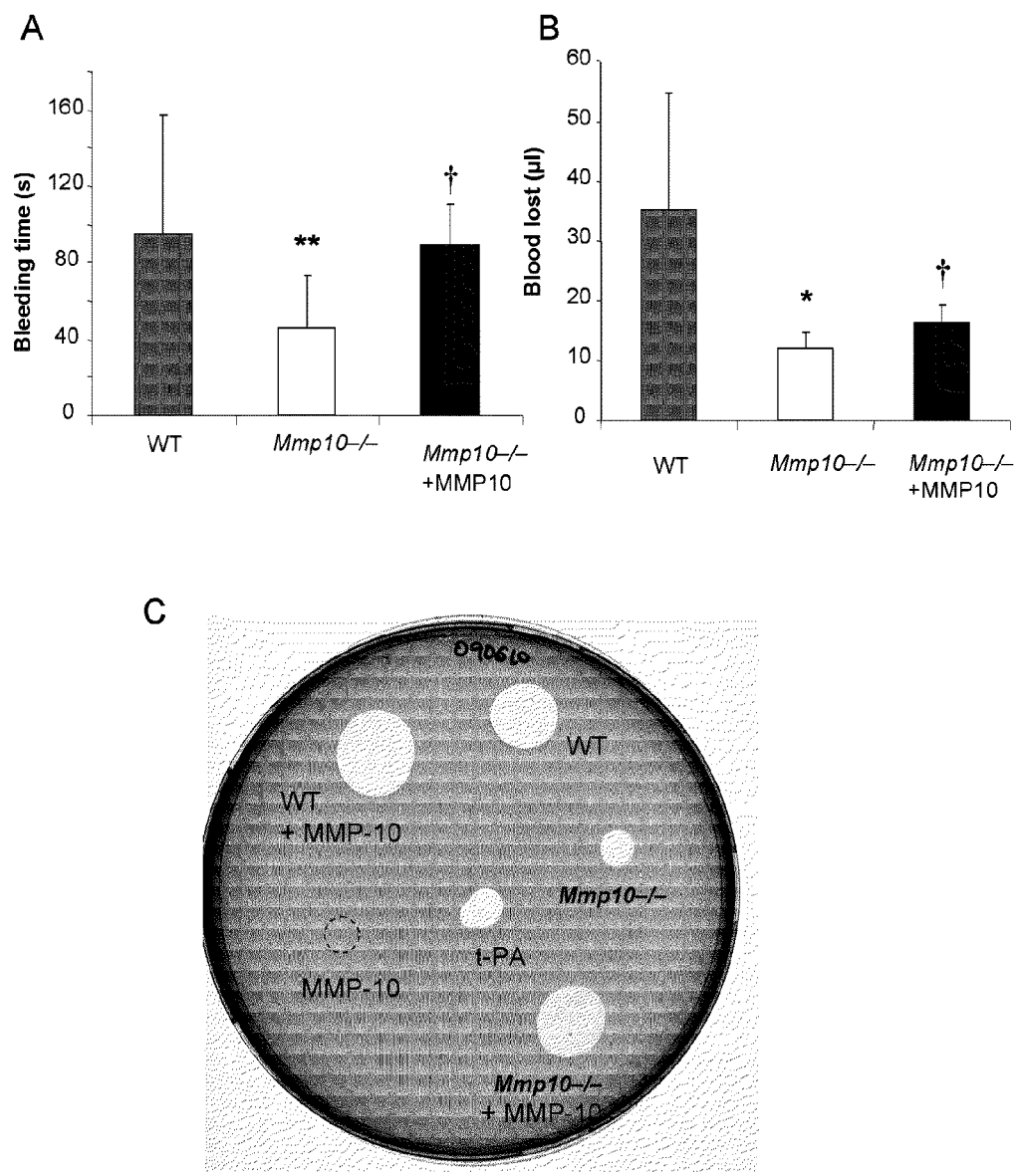
FIG. 7. Mmp10$^{-/-}$ mice exhibit haemostasis alteration. Panel A: Bleeding times of wild-type (WT, n=15), Mmp10$^{-/-}$ (n=15) and Mmp10$^{-/-}$ injected with active human recombinant MMP-10 (200 ng, n=6) (Mmp10$^{-/-}$ +MMP-10) (*"p<0.01). Panel B: blood lost (μl of blood) in the same groups of animals. A significant reduction was observed in the Mmp10$^{-/-}$ group (*p<0.05). Both parameters were reverted after administration of human recombinant MMP-10 (200 ng) († p<0.05 vs Mmp10$^{-/-}$). Panel C: Fibrinolytic activity of plasma euglobulins from WT and Mmp10$^{-/-}$ on fibrin plates (n=3). Plasma euglobulins from Mmp10$^{-/-}$ animals showed decreased lytic areas as compared with WT. Addition of active MMP-10 (200 nM) in both plasma euglobulins, increased the fibrin lysis although the effect was higher in euglobulins from Mmp10$^{-/-}$. 1 U/mL of tPA was used as positive control.

Tail tip transection bleeding time of Mmp10$^{-/-}$ mice was significantly shorter than WT (44.0±24.4 s vs 98.9±64.1 s) and the blood lost significantly reduced (12.1±2.5 μl vs 35.1±29.6 μl). Injection (i.v.) of active recombinant human MMP-10 (200 ng) normalized the bleeding time and increased the blood lost in Mmp10$^{-/-}$ mice (89.4±21.3 s and 15.4±3.2 μl) without affecting platelet count (FIGS. 7A and 7B). These results suggest that MMP-10 plays a role on haemostasis in vivo.

Regarding to the effect of MMP-10 on fibrinolysis, although fibrin lytic areas were evident in both groups, a significant reduction in fibrinolytic activity was observed in Mmp10$^{-/-}$ mice. Addition of recombinant MMP-10 (200 nM) increased euglobulin fibrinolytic activity specially in Mmp10$^{-/-}$ animals, confirming an abnormal hypofibrinolytic state in the absence of MMP-10 that can be restored by addition of the metalloproteinase (FIG. 7C).

Example 7

Effect of MMP-10 on Carotid Thrombosis

We conducted several in vivo experiments to assess more directly the effect of MMP-10 on arterial thrombosis by using a classic laser-induced carotid model.

Methods

Murine Carotid Artery Laser Thrombosis Model

Laser induced arterial injury was performed in 8 to 10 week old WT and Mmp10$^{-/-}$ male mice, which were anaesthesized with a mixture of 50 mg/Kg ketamine and 10 mg/Kg xylazine. Prior to rose Bengal (100 mg/kg), 200 μl of vehicle or recombinant human MMP-10 (200 ng) previously activated by 24 h incubation at 37° C., were injected by ocular plexus. The left carotid artery was carefully exposed and a pulse Doppler flow probe (diameter: 0.5 mm, Transonic, Sidney, Australia) was placed around the artery. The mid portion of the common carotid artery was then illuminated with a 1.5-mW green light laser (540 nm; Melles Griot Inc) and blood flow was recorded for 2 h.

Statistical Analysis

Data from mice were analysed by the non-parametric Kruskall-Wallis test followed by the Mann-Whitney U test to compare different experimental groups. Continuous variables were expressed as mean±SD.

Results

Figure 8:
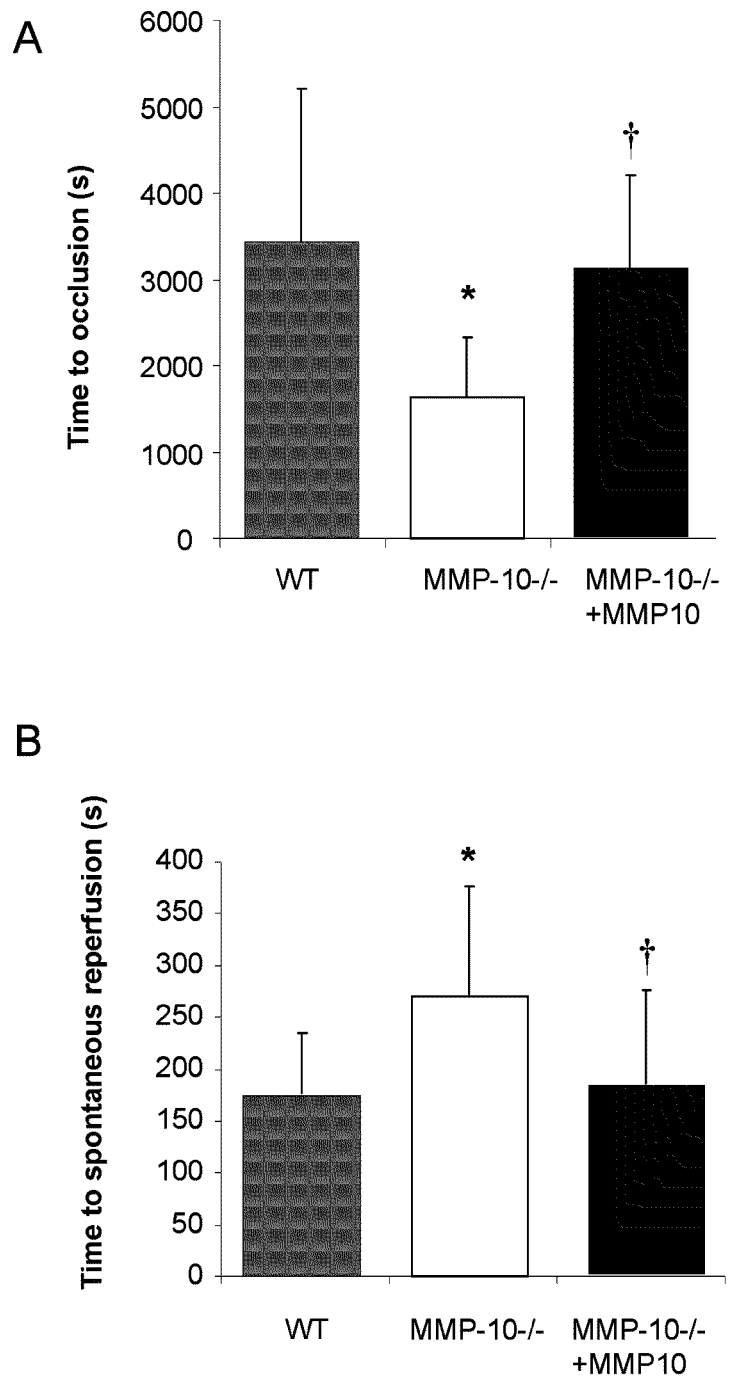
FIG. 8. Effect of MMP-10 on laser-induced carotid thrombosis model. Panel A: time to occlusion was significantly decreased in Mmp10 as compared to WT (n=10, *p<0.05). Panel B: time to lysis was clearly increased in Mmp10$^{-/-}$ as compared to WT (n=10, *p<0.05). Both parameters were reverted after administration of active human recombinant MMP-10 (200 ng) (n=6, † p<0.05 vs Mmp10$^{-/-}$).

As shown in FIG. 8A, the formation of an occlusive thrombus occurred faster in Mmp10$^{-/-}$ mice as compared to WT (1639±686 s vs 3408±1778 s) and thrombus lysis was significantly delayed (270±107 s vs 174±60 s) (FIG. 8B). Interestingly, i.v. administration of active recombinant human MMP-10 (200 ng) to Mmp10$^{-/-}$ mice reversed both endpoints, i.e., promoting faster occlusion (2926±1069 s, n=6, p<0.05) and delayed reperfusion (183±92 s, n=6, p<0.05).

EXAMPLE 8

Effect of MMP-10 on Thrombin-induced Stroke

An experimental stroke model was induced in WT and Mmp10$^{-/-}$ mice by in situ thrombin injection (1 U/µl) in the middle cerebral artery.

Methods

Mouse Model of In Situ Thromboembolic Stroke and Reperfusion

Animals (4 months old) were anaesthetised with 2.5% isoflurane. A catheter was inserted into the tail vein to allow the intravenous administration (200 µL) of saline, tPA (10 mg/kg) or active recombinant human MMP-10 (200 ng). Body temperature was maintained with a rectal probe at 37±0.5° C. throughout the surgical procedure using a feedback-regulated heating system.

Thrombin clot formation was performed as previously described (Orset et al., Stroke 2007;38(10):2771-8) using a micropipette filled with 1 µL of purified murine alpha-thrombin (1 NIH U/µl or 2 U/µl, to induce more stable clot) by applying negative pressure. Mice were placed in a stereotaxic device, the skin between the right eye and the right ear was incised, and the temporal muscle was retracted. A small craniotomy was performed, the dura excised, and the middle cerebral artery (MCA) was exposed. The pipette was introduced into the lumen of the MCA bifurcation and thrombin was pneumatically injected by applying positive pressure to induce the formation of a clot in situ. The pipette was removed 10 minutes after the injection to allow clot stabilisation.

To induce thrombolysis, tPA (10 mg/kg; Actilyse) was intravenously injected (tail vein, 10% bolus, 90% perfusion during 40 minutes) 20 minutes after the injection of thrombin. The control group received the same volume of saline under identical conditions. Cerebral blood velocity was determined by laser Doppler Flowmetry using a fiberoptic probe (Oxford Optronix) glued to the skull in the MCA territory. Cerebral blood velocity was measured before the injection of thrombin (100% baseline) and throughout the experiment (75 minutes).

Assessment of Lesion Volume and Histology

After 24 hours, mice were euthanized and brains removed and frozen in isopentane. Cryostat-cut coronal brain sections (20 µm) were stained with thionine and analysed with an image analyser (Image J, National Institutes of Health, USA). For volume analysis, one section out of every 10 was stained and lesion (nonstained) areas were measured (covering the entire lesion). To identify the presence of haemorrhage after tPA (1 and 10 mg/kg) or MMP-10 (200 ng), treatments (if any), a second set of cryostat cut coronal brain sections (20 µm) were stained using the Perls' Prussian blue method and counterstained with nuclear fast red to reveal iron overload (Hematognost Fe, Merck).

TAFI Activity in vivo

To assess the in vivo effect of MMP-10 on TAFI activity, plasma samples were taken from Mmp10$^{-/-}$ and WT animals before and 24 h after experimental stroke. TAFI activity was determined by chromogenic assay (Pefakit, Pentapharma) (Mosnier et al., Thromb Haemost. 1998;80(5):829-35)

Statistical Analysis

Data from mice were analysed by the non-parametric Kruskall-Wallis test followed by the Mann-Whitney U test to compare different experimental groups. Continuous variables were expressed as mean±SD.

Results

Effect of MMP-10 on in situ Thromboembolic Stroke Model

Figure 9:
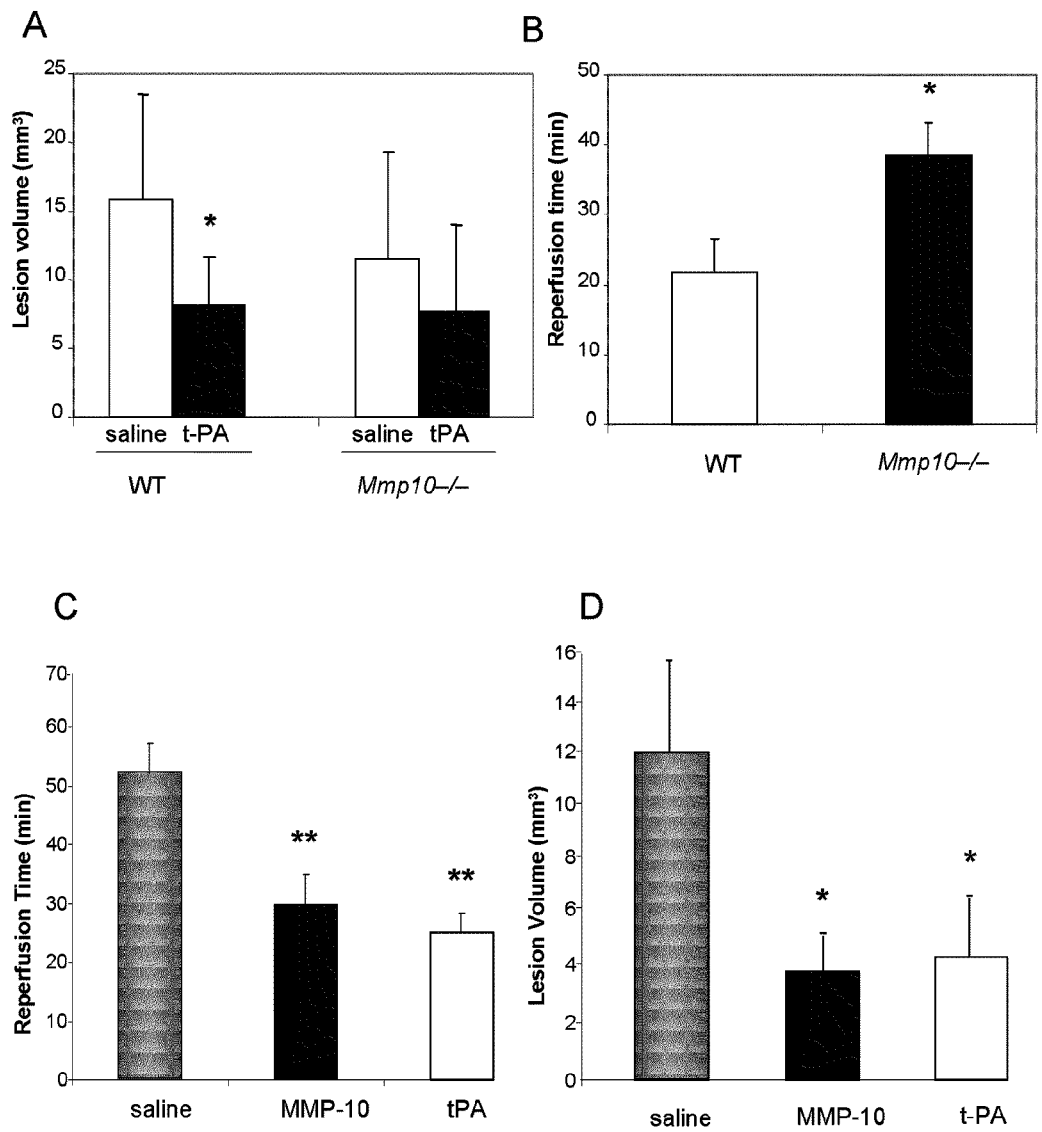
FIG. 9. Effect of MMP-10 on ischemic stroke model. Panel A: Ischemic lesion volume in WT and Mmp10$^{-/-}$ mice after treatment with saline and tPA (n=10). Panel B: Reperfusion time in WT and Mmp10$^{-/-}$ mice after tPA treatment, measured by laser Doppler sonography. The time for reperfusion was significantly delayed in Mmp10$^{-/-}$ mice as compared to WT (*p<0.05). Panel C: Similarly, improved reperfusion time after MMP-10 or tPA treatment in WT mice as compared to controls (n=10, **p<0.01). Panel D: Reduction in the volume of the lesion after treatment with tPA or MMP-10 (n=10, *p<0.05).

All animals showed infarct areas restricted to the cortex without differences in the mean lesion volume between WT and Mmp10$^{-/-}$ mice (15.7±7.8 mm$^3$ vs 11.5±7.6 mm$^3$). Average reduction in cerebral blood flow was similar in both genotypes (WT: 81.8±11.5%; Mmp10$^{-/-}$: 74.8±14.6%). However, Mmp10$^{-/-}$ animals exhibited a significant reduction in the frequency of spontaneous reperfusion (28.6% vs 68.7%, p<0.05). Additional experiments with recombinant tPA-based thrombolytic therapy (10 mg/Kg) showed a decreased infarct volume in WT mice compared to control animals reperfused with saline (45% reduction, p<0.05). In contrast, Mmp10$^{-/-}$ mice treated with tPA showed no significant changes in infarct area compared with null mice receiving saline (FIG. 9A), together with a significant delay in reperfusion as compared with WT (38.6±4.7 min vs 21.9±4.7 min, p<0.05) (FIG. 9B).

To analyse the thrombolytic effect of MMP-10 infusion, we performed the stroke model increasing the thrombin concentration to generate a more stable clot. After injecting 2 U/µl thrombin, only 3/10 WT animals showed spontaneous reperfusion after saline infusion. Under these conditions, 30 WT animals were divided into 3 groups (n=10) that received saline, tPA (10 mg/Kg), or active recombinant human MMP-10 (200 ng) through the tail vein. As expected, treatment with tPA significantly shortened reperfusion time (25±3 min vs 52±5 min, p<0.01). Interestingly, MMP-10 administration also significantly reduced reperfusion time (29.6±5.3 min, p<0.01 vs saline) without differences with tPA (FIG. 9C). Moreover, infarct volume in both tPA and MMP-10 groups was significantly reduced (70% and 74% respectively, p<0.05) as compared with control. These data indicate that MMP-10 shows similar efficacy to tPA in terms of shortening reperfusion time and reducing infarct volume (FIG. 9D).

Effects of MMP-10 on Haemorrhages and Bleeding Time

Figure 10:
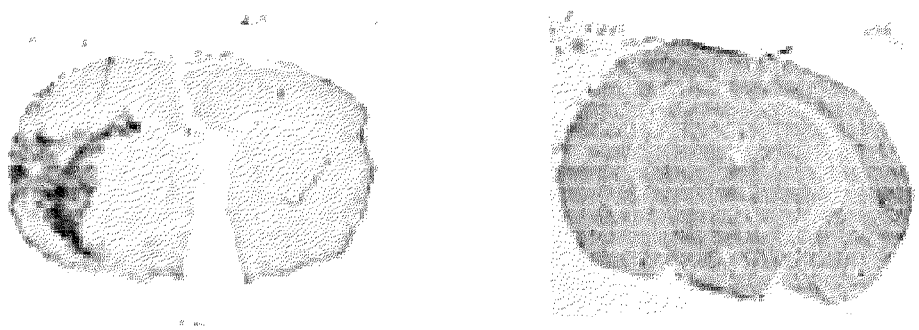
FIG. 10. Assessment of haemorrhage and bleeding time after thrombolysis on ischemic stroke model. Panel A: Macrophotograph of positive haemorrhage control performed by injecting collagen type VII (left) and a representative section of ishemic stroke lesion without evidence of intracranial haemorrhage. Panel B: Reduced bleeding time of WT animals after active MMP-10 (200 ng, n=6) infusion as compared to tPA (10 and 1 mg/Kg, n=5), although still higher than saline (n=5) (†† p<0.01 vs tPA; **p<0.01 vs saline).
Figure 10:
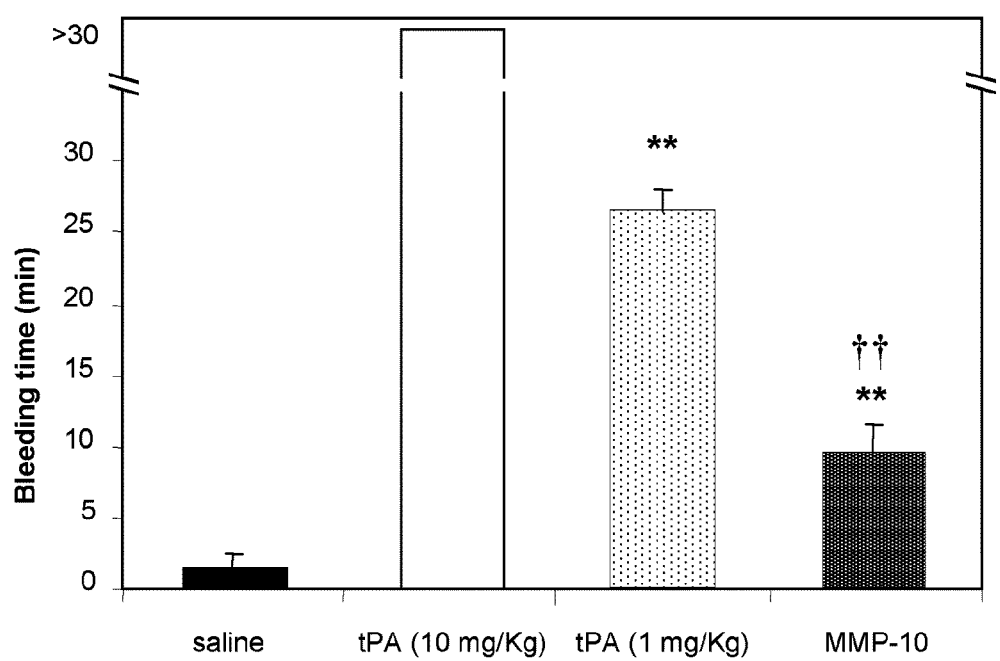

To determine if MMP-10 confers advantages over tPA, we analysed haemorrhage by Perls' staining in cryostat brain sections, and also determined bleeding time in WT animals injected via ocular plexus with tPA, active recombinant human MMP-10, or saline as described above. No evidence of intracranial haemorrhage was observed under these conditions in any of the animals tested as compared with positive controls performed with collagenase type VII (FIG. 10A). However, WT animals (n=5) receiving experimental dose of tPA (10 mg/Kg) exceeded the maximal bleeding time allowed (30 min), whereas those injected with the experimental dose of MMP-10 (200 ng, n=6) showed a much shorter bleeding time (10 min, p<0.01) although still longer than controls. When the dose of tPA was reduced to therapeutic levels in humans (1 mg/Kg) still three out of five animals exceeded 30 min and two animals stopped bleeding at 25 and 28 min (FIG. 10B).

Effect of MMP-10 on TAFI in vivo

Figure 11:
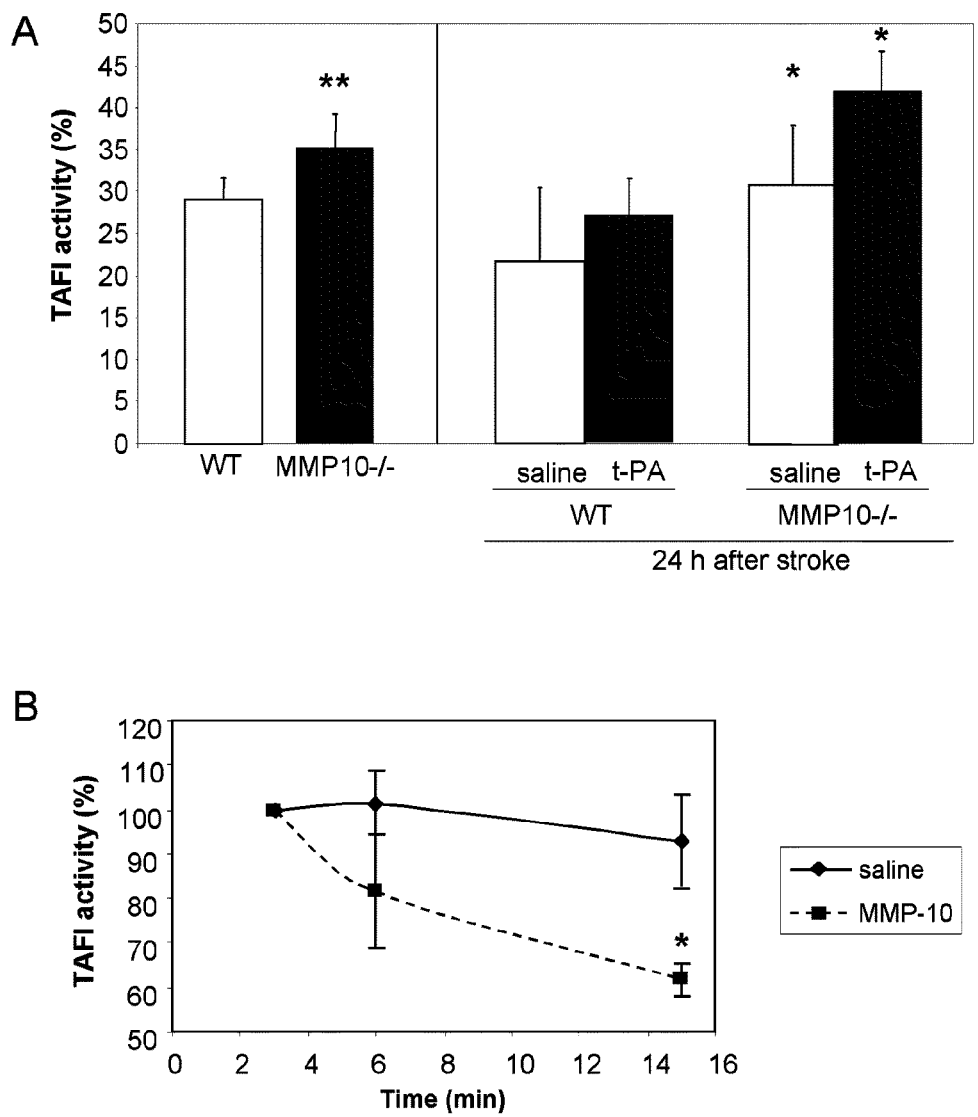
FIG. 11. In vivo circulating TAFI activity. Panel A: plasma TAFI activity measured with chromogenic substrate (Pefakit) in Mmp10$^{-/-}$ was significantly higher than WT at baseline and 24 h after stroke in saline or tPA-treated groups. *p<0.05 vs WT, n=10. Panel B: Fast inhibition of active TAFI generation after treatment with active MMP-10 (200 ng) in WT mice (n=3). *p<0.05 vs saline.

As shown in FIG. 11A, Mmp10$^{-/-}$ mice exhibited higher basal TAFI activity than did WT animals (35.2±3.9% vs 29.1±2.5%, p<0.01). TAFI activity was also increased after experimental stroke, suggesting that MMP-10 impairs TAFI activity in vivo.

Moreover, WT animals (n=6) were injected with active recombinant human MMP-10 or saline, and plasma samples were collected at different times (0-15 min) to measure TAFI activity. FIG. 11B showed a significant reduction in TAFIa generation as soon as 15 min after MMP-10 injection, suggesting in vivo lower TAFIa generation in the presence of MMP-10.

Conclusion

The role of MMP-10 in vivo has been first demonstrated by a significant 2-fold shortening of the mouse tail bleeding time in Mmp10$^{-/-}$ mice, and its restoration after intravenous injection of MMP-10, indicating a role in normal haemostasis. Further, this profibrinolytic effect of MMP-10 on arterial thrombus formation has been further confirmed in vivo using 2 different experimental models: carotid thrombosis and ischemic stroke. As expected, we observed faster carotid thrombus formation and significantly delayed clot lysis in Mmp10$^{-/-}$ mice, both restored by intravenous administration of MMP-10. This suggests that there is limited fibrinolysis in the absence of active MMP-10, shifting the haemostatic equilibrium towards hypofibrinolysis, as shown by earlier clot formation and delayed fibrinolysis in this thrombosis model and low overall euglobulin fibrinolytic activity in the absence of MMP-10.

Profibrinolytic activity of MMP-10 has also been evident in thrombin-induced murine stroke model, where intravenous administration of 200 ng MMP-10 has showed a thrombolytic efficacy similar to 10 mg/Kg tPA, in terms of infarct volume and reperfusion time. The relevance of MMP-10 as endogenous profibrinolytic agent could be clearly demonstrated by the lower reperfusion rate observed after clot formation in the middle cerebral artery (MCA) of Mmp10$^{-/-}$ mice. Furthermore, noticing that this is one of the few experimental models where beneficial effects of tPA can be shown, in terms of improving cerebral reperfusion and reducing ischemic brain lesion damage (Orset C, et al. *Stroke* 2007;38(10):2771-8), it should be pointed out that thrombolysis with tPA failed to reduce lesion volume and reperfusion time in Mmp10$^{-/-}$ mice.

Finally, it should be noticed that significant improvement in arterial reperfusion and reduction in the volume of brain lesion obtained in MMP-10 treated mice has been achieved with no bleeding complications, particularly intracraneal haemorrhage. In contrast, supra-therapeutic and therapeutic doses of tPA has showed off-scale bleeding times (100% and 60%, respectively), that were not observed in mice treated with MMP-10, suggesting a significant advantage over tPA. Such a safe therapy might be particularly advantageous in the treatment of acute stroke because conventional thrombolysis is inherently associated with increased risk of intracranial haemorrhages. Whether MMP-10 could also act as adjuvant of the fibrinolytic effect of tPA, allowing for a reduced dose administration, requires additional investigation.

In conclusion, our study demonstrates MMP-10 is a new profibrinolytic agent in vivo and in vitro, and unveils that TAFI inactivation is at least one of the mechanisms involved. We have demonstrated that MMP-10 markedly reduces brain lesion in a murine model of stroke, indicating that may be, either alone or as fibrinolytic adjuvant, a powerful agent for the treatment of cerebrovascular events in humans.

The invention claimed is:

1. A method for thrombolytic treatment and therapy comprising administering to a patient in need thereof a therapeutically effective quantity of a matrix metalloproteinase-10 (MMP-10).

2. The method according to claim 1, further comprising administering to the patient in need thereof a therapeutically effective quantity of a plasminogen activator.

3. The method according to claim 2, wherein the MMP-10 and the plasminogen activator are simultaneously, separately or sequentially administered.

4. The method according to claim 2, wherein the plasminogen activator is selected from the group consisting of tPA tissue plasminogen activator, uPA urokinase activator, streptokinase, staphylokinase, a derivative thereof capable of activating plasminogen, and a fragment thereof capable of activating plasminogen.

5. The method according to claim 4, wherein the plasminogen activator is selected from the group consisting of tPA, a derivative thereof capable of activating plasminogen, and a fragment thereof capable of activating plasminogen.

6. The method according to claim 4, wherein the plasminogen activator is selected from the group consisting of uPA, a derivative thereof capable of activating plasminogen, and a fragment thereof capable of activating plasminogen.

7. The method according to claim 2, for thrombolytic treatment and therapy of ischemic stroke.

8. The method according to claim 7, wherein the ischemic stroke is a thromboembolic stroke.

9. The method according to claim 8, wherein the thromboembolic stroke is an atherosclerotic thromboembolic stroke.

10. The method according to claim 2, for thrombolytic treatment and therapy of carotid artery thrombosis.

11. The method according to claim 1, for thrombolytic treatment and therapy of ischemic stroke.

12. The method according to claim 11, wherein the ischemic stroke is a thromboembolic stroke.

13. The method according to claim 12, wherein the thromboembolic stroke is an atherosclerotic thromboembolic stroke.

14. The method according to claim 1, for thrombolytic treatment and therapy of carotid artery thrombosis.

\* \* \* \* \*

```
SEQUENCE LISTING

<160> NUMBER OF SEQ ID NOS: 2

<210> SEQ ID NO 1
<211> LENGTH: 21
<212> TYPE: DNA
<213> ORGANISM: Artificial Sequence
<220> FEATURE:
<223> OTHER INFORMATION: Synthetic Construct

<400> SEQUENCE: 1
atgatgcatc ttgcattcct t                                            21

<210> SEQ ID NO 2
<211> LENGTH: 21
<212> TYPE: DNA
<213> ORGANISM: Artificial Sequence
<220> FEATURE:
<223> OTHER INFORMATION: Synthetic Construct

<400> SEQUENCE: 2
gcaatgtaac cagctgttac t                                            21
```